(12) United States Patent
Leventis et al.

(10) Patent No.: US 9,550,846 B2
(45) Date of Patent: Jan. 24, 2017

(54) FLEXIBLE TO RIGID NANOPOROUS POLYURETHANE-ACRYLATE (PUAC) TYPE MATERIALS FOR STRUCTURAL AND THERMAL INSULATION APPLICATIONS

(71) Applicant: The Curators of the University of Missouri, Columbia, MO (US)

(72) Inventors: Nicholas Leventis, Rolla, MO (US); Chariklia Sotiriou-Leventis, Rolla, MO (US); Abhishek Bang, Rolla, MO (US)

(73) Assignee: The Curators of the University of Missouri, Columbia, MO (US)

(*) Notice: Subject to any disclaimer, the term of this patent is extended or adjusted under 35 U.S.C. 154(b) by 116 days.

(21) Appl. No.: 14/208,892

(22) Filed: Mar. 13, 2014

(65) Prior Publication Data
US 2015/0266983 A1 Sep. 24, 2015

Related U.S. Application Data

(60) Provisional application No. 61/851,814, filed on Mar. 13, 2013.

(51) Int. Cl.
| | |
|---|---|
| C08F 122/10 | (2006.01) |
| C07C 271/28 | (2006.01) |
| C08F 222/10 | (2006.01) |
| B01J 31/22 | (2006.01) |
| C08G 101/00 | (2006.01) |

(52) U.S. Cl.
CPC .......... C08F 122/10 (2013.01); B01J 31/2208 (2013.01); C07C 271/28 (2013.01); C08F 222/10 (2013.01); B01J 2531/42 (2013.01); C07C 2102/42 (2013.01); C08F 2222/1066 (2013.01); C08G 2101/0091 (2013.01)

(58) Field of Classification Search
CPC .................. C08F 122/10; C08F 222/10; C08F 2222/1066; C07C 271/28; C08G 2101/0091
See application file for complete search history.

(56) References Cited

U.S. PATENT DOCUMENTS

| | | | | |
|---|---|---|---|---|
| 4,690,870 A | * | 9/1987 | Okita | .................. G11B 5/7022 252/62.54 |
| 4,734,319 A | * | 3/1988 | Doi | ......................... C09D 5/24 427/214 |
| 2011/0087041 A1 | * | 4/2011 | Ishiyama | .............. C07C 269/02 560/25 |
| 2012/0268828 A1 | * | 10/2012 | Chen | ............... B29D 11/00317 359/642 |

* cited by examiner

*Primary Examiner* — Rabon Sergent
(74) *Attorney, Agent, or Firm* — Bassam S. Nader; Brannon Sowers & Cracraft PC

(57) ABSTRACT

Novel urethane-acrylate (UAC) Star monomers and polyurethane-acrylate (PUAC) aerogel polymers derived therefrom are described herein, along with other novel, related monomers and polymers. Also described herein are processes for preparing the UAC Star monomers, the PUAC aerogel polymers, and the other related monomers and polymers. The PUAC and related polymers herein are useful in various applications including in structural and thermal insulation.

29 Claims, 17 Drawing Sheets

FLEXIBLE TO RIGID NANOPOROUS POLYURETHANE-ACRYLATE (PUAC) TYPE MATERIALS FOR STRUCTURAL AND THERMAL INSULATION APPLICATIONS

GOVERNMENT RIGHTS

This invention was made with Government support under Grant No. CHE-0809562 awarded by the National Science Foundation and Grant No. W911NF-10-1-0476 awarded by the Army Research Office. The U.S. government has certain rights in the invention.

TECHNICAL FIELD

The present invention relates, inter alia, to structural insulation materials, thermal insulation materials, and similar materials. More specifically, the present invention relates to a series of nanoporous polyurethane-acrylate type materials and similar materials for applications in structural insulation, thermal insulation, and the like.

BACKGROUND AND SUMMARY OF THE INVENTION

In one embodiment, the present invention discloses a series of nanoporous polyurethane-acrylate (PUAC) type materials for applications in structural insulation, thermal insulation, and the like. In another embodiment, the present invention discloses a series of urethane-acrylate (UAC) Star monomers, which are monomeric precursors for the preparation of the PUAC materials. In yet another embodiment, the present invention discloses one or more processes for the conversion of the UACs to their corresponding PUACs. In yet another embodiment, the present invention discloses methods of use of the PUACs as aerogel materials for applications in structural insulation, thermal insulation, and the like.

Aerogels have been known as three-dimensional lightweight porous materials formed by aggregation of nanoparticles, wherein the thickness dimension may vary greatly (from nanometers to meters) such that in some cases they may be viewed as quasi-two-dimensional objects. High surface areas and open porosities have been reported as being two of the most attractive properties for applications in thermal insulation, drug delivery, catalysis, and other applications. Aerogels are believed to have been first reported in 1931 by Kistler, who is believed to have introduced supercritical fluid (SCF) drying as a means to retain the network morphology of wet-gels into the final dry objects. Most post-Kistler attention appears to have focused on silica aerogels. Organic aerogels seem to have started getting attention after the synthesis of resorcinol-formaldehyde (RF) aerogels.

For a number of years, polymer- and RF-aerogels were almost synonymous terms. In the last few years, however, research on other polymer-based aerogels seems to have gained significant momentum. It is believed that the reasons include well-defined chemistry, molecular design flexibility, readily available raw materials, and the excellent mechanical, thermal, chemical, and other properties of these polymers.

In another embodiment, described herein are polymer aerogels obtained by using polyurethane-acrylate (PUAC) chemistry. PUAC polymers have been popular in the automotive and coating industries. It is believed that this is so because PUAC polymers incorporate properties of both polyurethanes and polyacrylates, and because they can be prepared easily by free-radical polymerization using UV light or heat. It has been observed that low density PUAC aerogels tend to be flexible, while higher density PUAC aerogels tend to possess greater stiffness and stronger mechanical properties.

It has been reported that flexible aerogels are interesting for a plethora of applications, illustratively, in planetary descent and landing (EDL) systems, thermal insulation, such as in sub-sea oil pipes (e.g., see http://www.aerogel.com/markets/subsea.html) and buildings (e.g., acoustic insulation), where flexibility and foldability are considered to be necessary properties. It has also been reported that the impressive strength-to-weight ratio of higher-density PUAC aerogels renders them attractive as energy absorbers for defense applications.

In another embodiment of the invention herein, thermally stable PUAC aerogels are described. In one aspect, the thermal stability of these PUAC aerogels can be as high as 300° C. In another aspect, the thermally stable PUAC aerogels are synthesized from inexpensive isocyanates and hydroxyl functionalized acrylates.

In another embodiment of the invention, described herein are polyurethane and polycarbonate aerogels, which are synthesized from urethane-acrylate or carbonate-acrylate star monomers. In one aspect, these star monomers are stable and easy to handle, as compared to highly-reactive isocyanates or phosgene. In another aspect, the raw materials used herein are inexpensive and readily available.

In another embodiment of the invention, described herein are inexpensive, multifunctional, light-weight, bendable nanoporous materials with high degree of flexibility. In one aspect, these materials may be prepared via easy, one-step synthesis methods, as will become apparent from the following discussion.

In another embodiment, as contemplated herein, the materials described in this invention may be useful as multifunctional thermal and acoustic insulating materials for buildings, sub-sea oil pipes, automobiles and aircraft, and as energy absorbers for anti-ballistic applications, such as, illustratively, armor and blast wave mitigation against improvised explosive devices (IEDs).

In another illustrative embodiment of the invention, the UAC Star monomers are compounds of the formula (I):

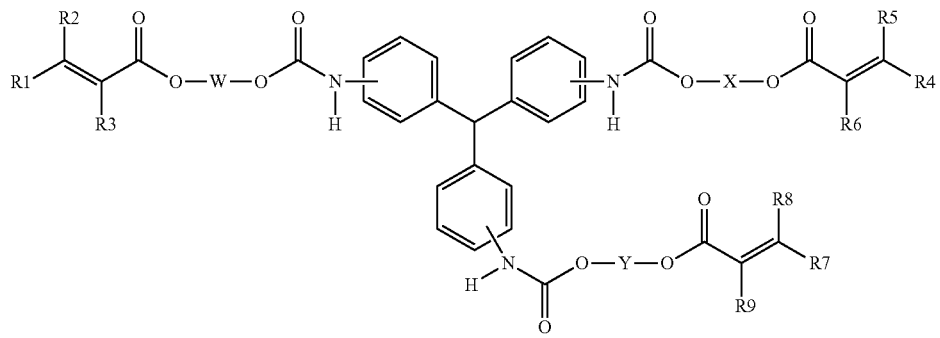

wherein the nitrogen atoms of the urethane moieties are independently attached to their respective aryl rings at the 2, 3, or 4-positions of the aryl rings; wherein each of W, X, and Y independently represents a $C_1$-$C_6$ straight chain alkyl group or a $C_1$-$C_6$ branched alkyl group; and wherein each of R1-R9 independently represents an H, a $C_1$-$C_6$ straight chain alkyl group or a $C_1$-$C_6$ branched alkyl group. It is understood that other related variations on the illustrative UAC Star monomers of formula (I) are contemplated herein, as will become apparent in the detailed discussion below.

In another illustrative embodiment of the invention, the PUAC polymers are compounds of the formula (II):

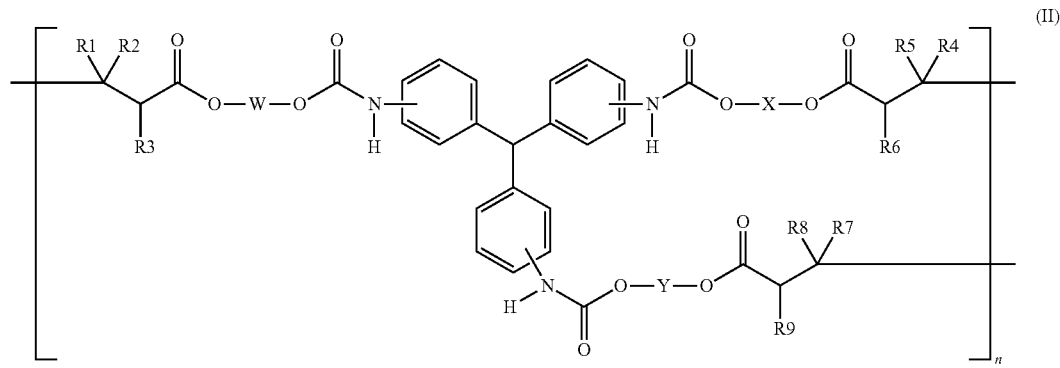

wherein the nitrogen atoms of the urethane moieties are independently attached to their respective aryl rings at the 2, 3, or 4-positions of the aryl rings; wherein each of W, X, and Y independently represents a $C_1$-$C_6$ straight chain alkyl group or a $C_1$-$C_6$ branched alkyl group; and wherein each of R1-R9 independently represents an H, a $C_1$-$C_6$ straight chain alkyl group or a $C_1$-$C_6$ branched alkyl group; and wherein n is an integer ranging upwardly from 2 upwardly to 100, 200, 500 or even higher. It is understood that other related variations on the illustrative PUAC polymers of formula (II) are contemplated herein, as will become apparent in the detailed discussion below.

In another embodiment of the invention, processes are described herein for the conversion of the UAC Star monomers to the PUAC aerogel polymers of the invention, as will be further described in the following discussion.

DETAILED DESCRIPTION

Figure 1:
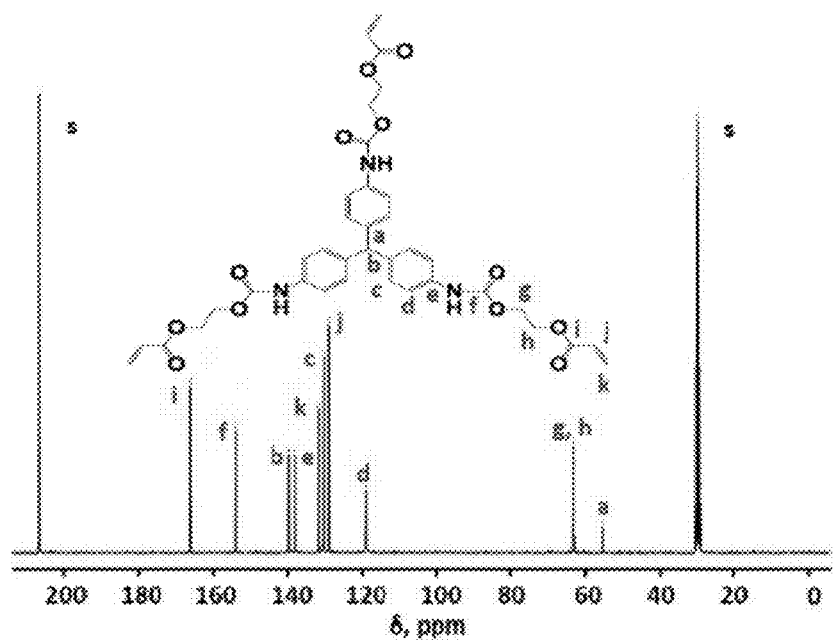
FIG. 1 shows the $^{13}C$ NMR spectrum of the UAC Star monomer of Example 1, in $CD_3COCD_3$.

In one embodiment of the invention, described herein are UAC Star monomers of the formula (I):

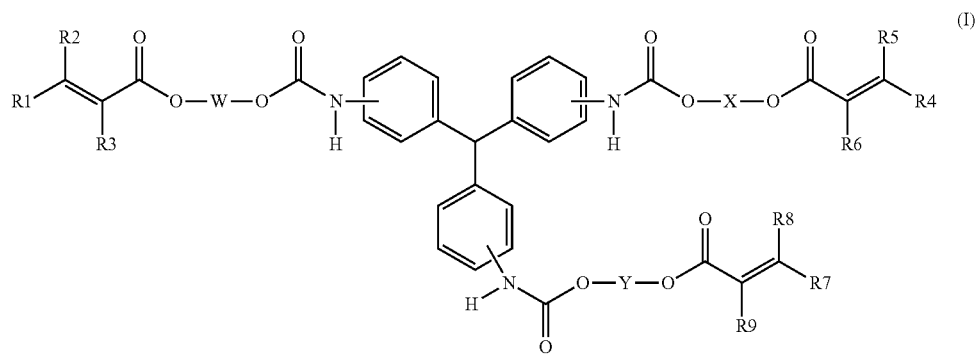
(I)

wherein the nitrogen atoms of the urethane moieties are independently attached to their respective aryl rings at the 2, 3, or 4-positions of the aryl rings; wherein each of W, X, and Y independently represents a $C_1$-$C_6$ straight chain alkyl

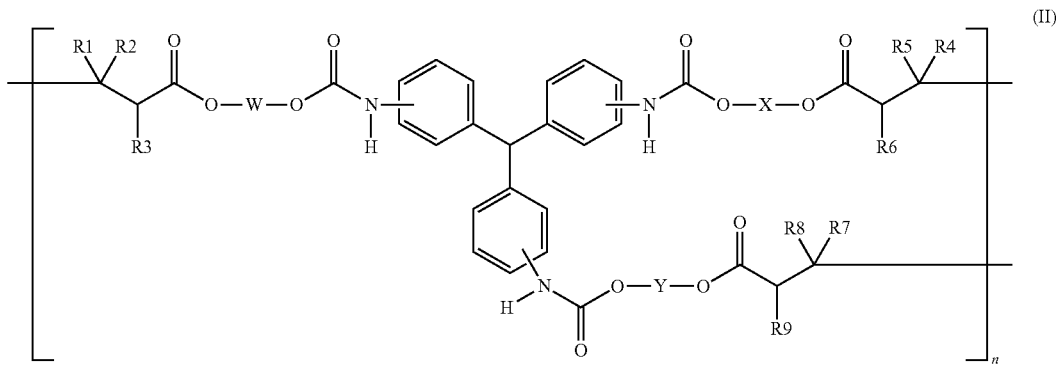
(II)

group or a $C_1$-$C_6$ branched alkyl group; and wherein each of R1-R9 independently represents an H, a $C_1$-$C_6$ straight chain alkyl group or a $C_1$-$C_6$ branched alkyl group. It is understood that other related variations on the illustrative UAC Star monomers of formula (I) are contemplated herein, as will become apparent in the detailed discussion below. In one illustrative example, it is contemplated herein that one or more of the urethane moieties of the foregoing UAC Star monomers of formula (I) may alternatively be replaced with carbonate groups, urea groups, and the like. The replacement of the urethane groups of the UAC Star monomers with carbonate groups or urea groups would provide carbonate-acrylate Star monomers or urea-acrylate Star monomers, respectively. In another illustrative example, it is contemplated herein that one or more of the aryl rings of the triarylmethane moiety of the UAC Star monomer of formula (I) may be substituted with any of a variety of substituent groups known in the art, illustratively, one or more $C_1$-$C_6$ straight chain alkyl group or $C_1$-$C_6$ branched alkyl group, one or more halogen atom, one or more alkoxy or alkylthio group, one or more ether or thioether group, one or more carboxy group, one or more ester group, one or more carboxamido group, one or more cyano group, one or more nitro group, and the like; or that one or more of the aryl rings of the triarylmethane moiety of the UAC Star monomer may be replaced with alternative aromatic or heteroaromatic rings other than benzene rings, including single-ring or fused-ring aromatics or heteroaromatics, wherein the alternative aromatic or heteroaromatic rings may be substituted with one or more of the foregoing substituents.

In another illustrative embodiment of the invention, described herein are PUAC polymers of the formula (II):

wherein the nitrogen atoms of the urethane moieties are independently attached to their respective aryl rings at the 2, 3, or 4-positions of the aryl rings; wherein each of W, X, and Y independently represents a $C_1$-$C_6$ straight chain alkyl group or a $C_1$-$C_6$ branched alkyl group; and wherein each of R1-R9 independently represents an H, a $C_1$-$C_6$ straight chain alkyl group or a $C_1$-$C_6$ branched alkyl group; and wherein n is an integer ranging upwardly from 2.

It is understood that other related variations on the illustrative PUAC polymers of formula (II) are contemplated herein, as will become apparent in the detailed discussion below. For example, one or more of the aryl rings of the triarylmethane moiety of the PUAC polymer of formula (II) may be substituted with any of a variety of substituent groups known in the art, similar to the substituent groups described in the previous paragraph in regard to the UAC Star monomers; or one or more of the aryl rings of the triarylmethane moiety of the PUAC polymer of formula (II) may be replaced with alternative aromatic or heteroaromatic rings other than benzene rings, including single-ring or fused-ring aromatics or heteroaromatics, wherein the alternative aromatic or heteroaromatic rings may be substituted with one or more of the foregoing substituents.

In another embodiment of the invention, a process for the preparation of the UAC Star monomers of formula (I) is described herein. In one illustrative example, the process comprises the step of reacting a tris(isocyanatoaryl)methane of formula (III) with one or more hydroxyalkyl acrylate of formula (IV), in a suitable solvent or mixture of solvents, following procedures known in the art, either with or without a catalyst, wherein the hydroxyl groups react with the isocyanato groups, to produce a UAC Star monomer of formula (I). Suitable solvents or mixtures of solvents for carrying out the process step include ketone solvents such as acetone, ester solvents such as ethyl acetate, and the like, or any other suitable solvents known to those skilled in the relevant art. In the case that a catalyst is used for the process step, suitable catalysts include various organometallic or organic catalysts known to those skilled in the relevant art, such as, illustratively, dibutyltin dilaurate (DBTDL). Following is an illustrative scheme of said process for preparing a UAC Star monomer of formula (I), wherein W=X=Y, R1=R4=R7, R2=R5=R8, and R3=R6=R9:

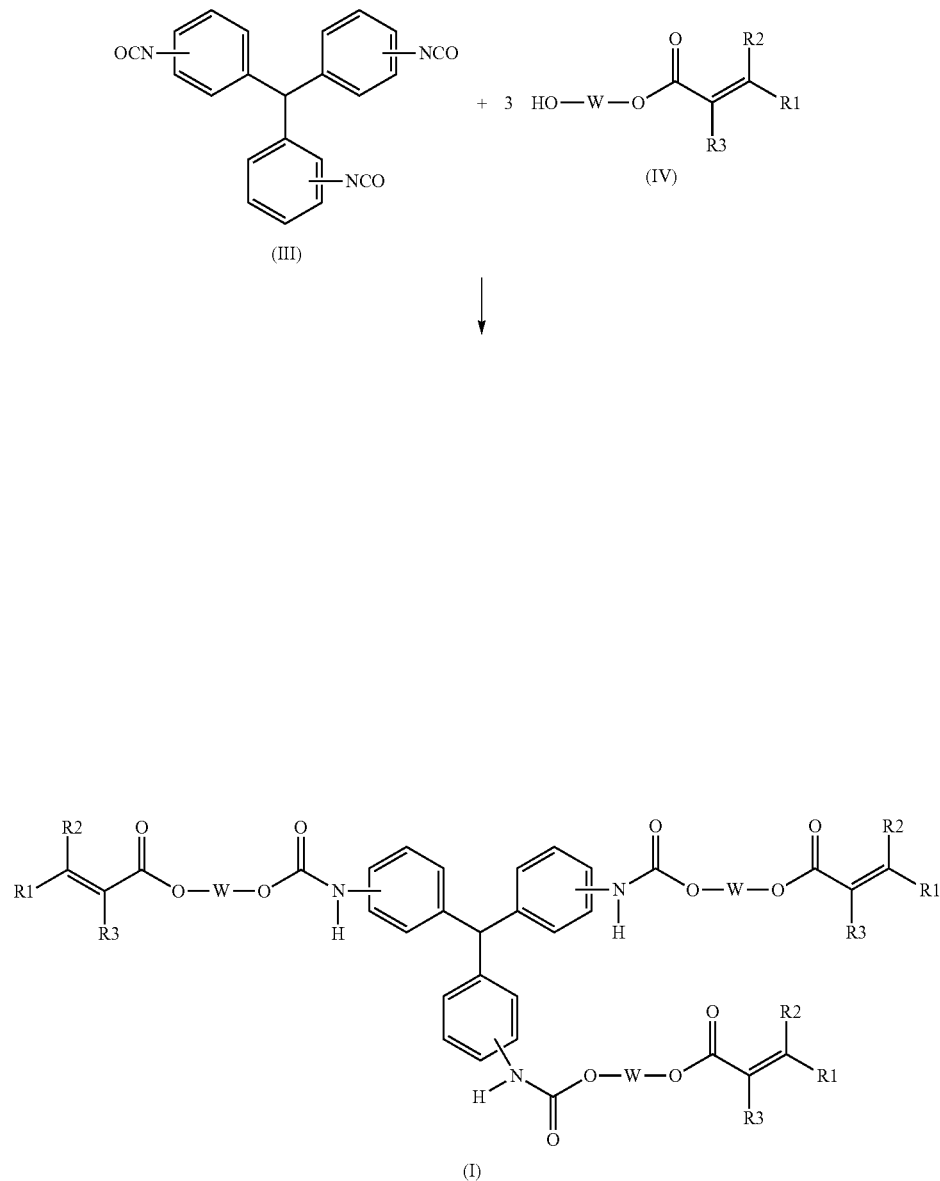

In another embodiment of the invention, a process for the preparation of the PUAC polymers of formula (II) is described herein. In one illustrative example, the process comprises the step of treating a solution of a UAC Star monomer of formula (I), in a suitable solvent or mixture of solvents, with a suitable polymerization catalyst, such as, illustratively, a free radical initiator. Suitable solvents or mixtures of solvents for carrying out the process step include ketone solvents such as acetone, ester solvents such as ethyl acetate, and the like, or any other suitable solvents known to those skilled in the relevant art. Suitable free radical initiators include any of a wide variety of agents known in the relevant art, such as, illustratively, the commonly used free radical initiator 2,2'-azobisisobutyronitrile (AIBN). In the following illustrative scheme of said process for the preparation of the PUAC polymers of formula (II), wherein W=X=Y, R1=R4=R7, R2=R5=R8, and R3=R6=R9, a solution of the UAC Star monomer (I) in a suitable solvent or mixture of solvents is treated with a catalytic amount of a free radical initiator, resulting in the formation of (II):

termed herein as chain extenders. These chain extenders are monomeric compounds capable of copolymerizing with the UAC Star monomers. Illustrative of these chain extenders are diacrylate compounds of the following general formula (V):

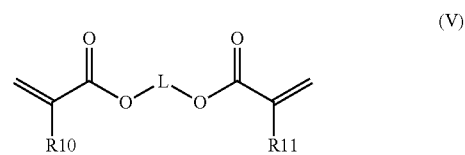

wherein L represents a linker group selected from $C_1$-$C_{12}$ straight chain or branched chain alkyl, alkoxyalkyl, alkoxycarbonylalkyl, and alkoxycarboxyalkyl; and wherein each of R10 and R11 independently represents an H, a $C_1$-$C_6$ straight chain alkyl group or a $C_1$-$C_6$ branched alkyl group.

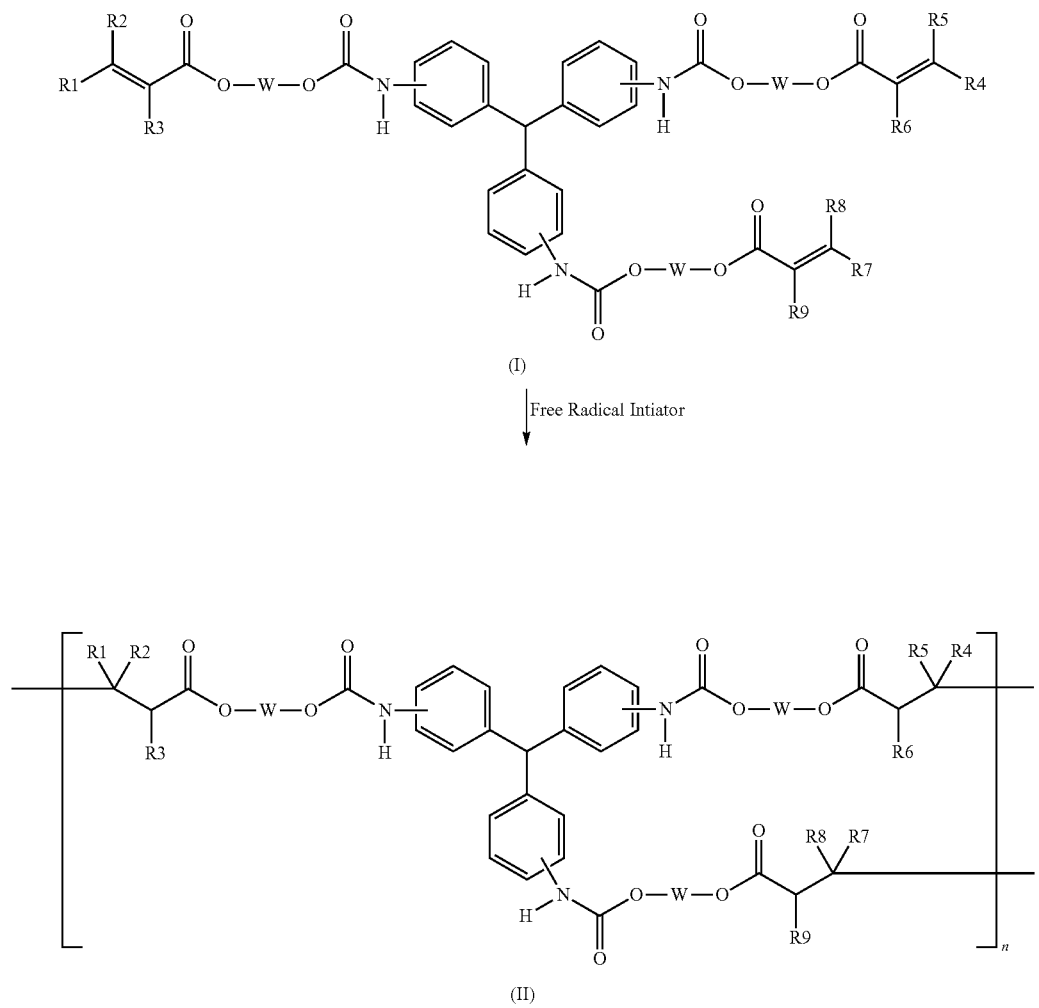

In another embodiment of the invention, a variation on the above process for generation of the PUAC polymers is described herein, which entails addition into the reaction mixture, prior to introduction of the polymerization catalyst (e.g., the free radical initiator), of one or more compounds In one aspect of the invention, the inclusion of these chain extenders in the polymerization step results in PUACs possessing favorable flexibility, thermal insulation and other properties, as will become apparent in the discussion below. Representative of the chain extenders of the invention are compounds of the following formulae; it is to be understood that these formulae are shown only for the purpose of illustration, that they are not to be construed as limiting the invention, and that other similar chain extenders well known to those skilled in the relevant art are contemplated herein:

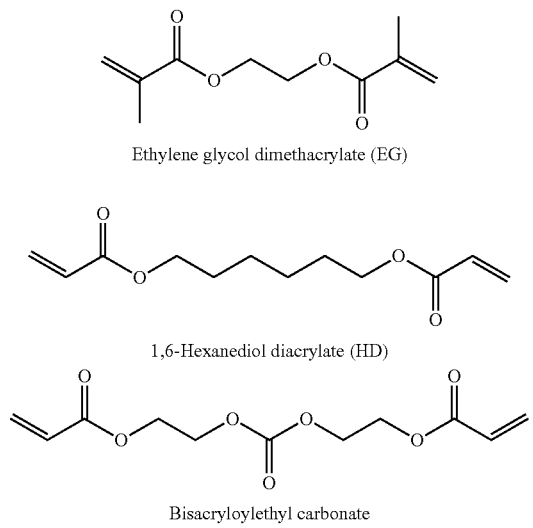

Ethylene glycol dimethacrylate (EG)

1,6-Hexanediol diacrylate (HD)

Bisacryloylethyl carbonate

In another embodiment of the invention, PUAC polymers are described herein that are obtained by the above polymerization process that includes the addition of one or more of the chain extenders to the UAC Star monomers, as described above. These PUAC polymers are similar in chemical structure to the chemical structure of the PUACs of formula (II), but include copolymerized chain extenders.

In another embodiment of the invention, a one-pot process for the preparation of the PUAC polymers of formula (II) starting from a tris(isocyanatoaryl)methane of formula (III) and one or more hydroxyalkyl acrylate of formula (IV) is described herein. In one illustrative example, the process comprises the step of reacting a tris(isocyanatoaryl)methane of formula (III) with one or more hydroxyalkyl acrylate of formula (IV), in a suitable solvent or mixture of solvents as described above, following procedures known in the art, either with or without a catalyst, to produce a solution of the corresponding UAC Star monomer of formula (I). This is followed directly, without isolation of (I), by treatment with a suitable polymerization catalyst, such as, illustratively, a suitable free radical initiator as described above, to produce (II). Following is an illustrative scheme of said one-pot process for the preparation of PUAC (II), wherein W=X=Y, R1=R4=R7, R2=R5=R8, and R3=R6=R9:

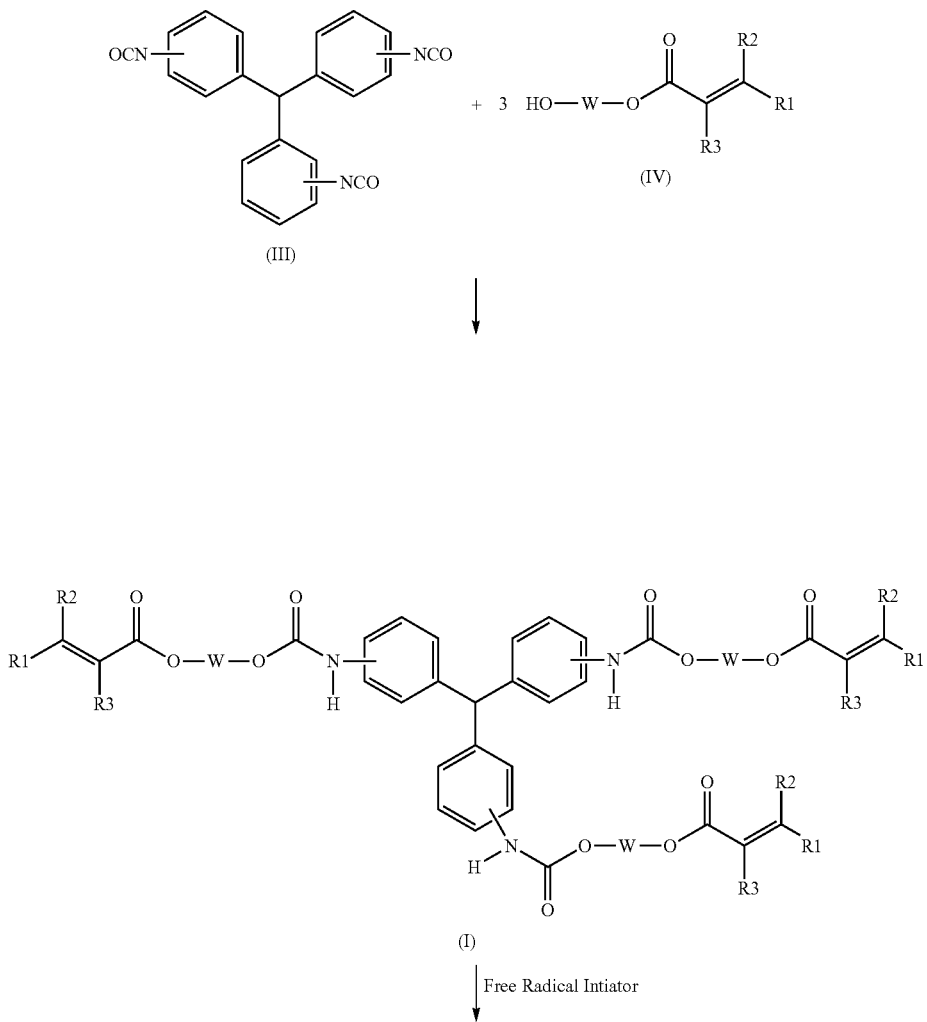

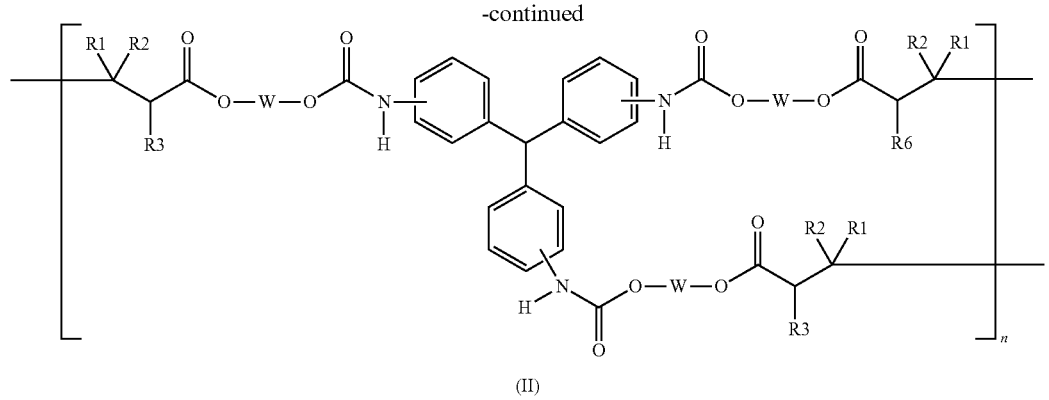

(II)

In another embodiment of the invention, an alternative one-pot process for the preparation of PUAC polymers is described herein. This alternative one-pot process is similar in all respects to the one-pot process described above for the preparation of the PUAC polymers of formula (II), but includes the addition into the reaction mixture, prior to introduction of the polymerization catalyst (e.g., the free radical initiator), of one or more of the chain extenders described above, thus resulting in PUACs that have copolymerized chain extender units incorporated therein.

In another embodiment of the invention, described herein are compounds that are derived by the electrocyclic (e.g., Diels-Alder) reaction in a suitable solvent of the alkene moiety of the hydroxyalkyl acrylate of formula (IV) with a diene, to produce the corresponding Diels-Alder adduct; wherein R1, R2, R3, and W are as defined in the foregoing. Suitable solvents for this reaction are the common solvents used in the art to carry out Diels-Alder reactions, such as toluene, the xylenes, and similar solvents. Illustrative of these compounds are those represented by formula (VI), which are obtained by reaction of the hydroxyalkyl acrylate of formula (IV) with cyclopentadiene to produce the corresponding norbornene, as shown in the following scheme:

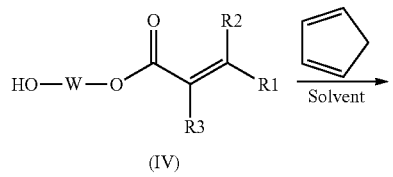

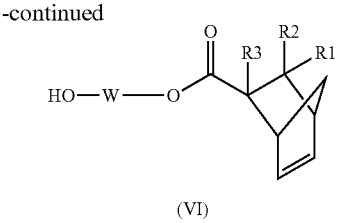

A specific example of the foregoing is the reaction of 2-hydroxyethyl acrylate (i.e., compound (IV) wherein W=CH$_2$CH$_2$; R1=R2=R3=H) with cyclopentadiene to produce norbornene adduct (VI) wherein W=CH$_2$CH$_2$; R1=R2=R3=H. It is to be understood that, as contemplated herein, other dienes may be used, including any of a plethora of non-cyclic and cyclic dienes known in the art.

In a further embodiment of the invention, Star monomers incorporating norbornene groups are described herein. These norbornene containing Star monomers are obtained by the reaction of the norbornene compounds (VI) with a tris(isocyanatoaryl)methane of formula (III) under conditions that are similar to those described above for the reaction of (III) with (IV). Illustrative of those Star monomers that incorporate norbornene groups are those represented by the formula (VII), which are obtained by the reaction of the norbornene compounds (VI), wherein R1=R2=R3=H, with a tris(isocyanatoaryl)methane of formula (III), as shown in the following scheme:

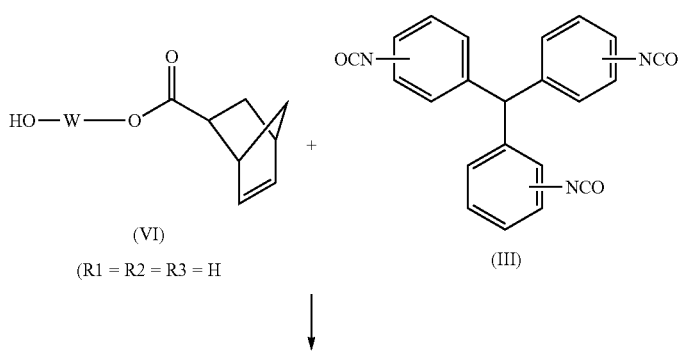

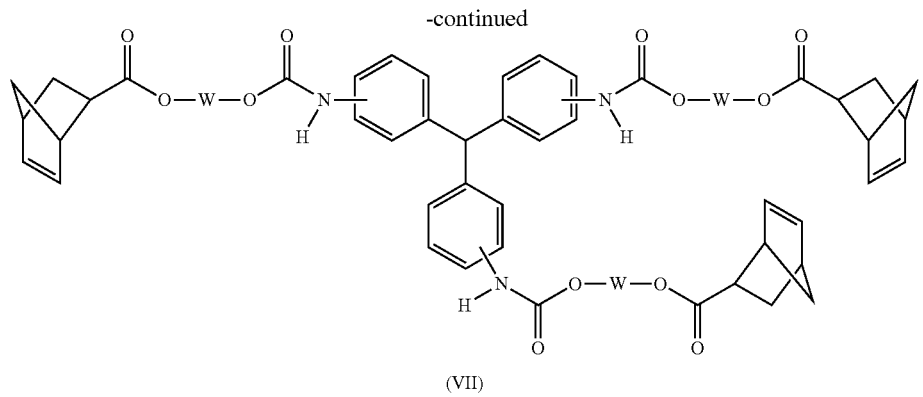

(VII)

In another embodiment of the invention, described herein are compounds that are derived by the electrocyclic (e.g., Diels-Alder) reaction in a suitable solvent of the alkene moieties of hydroxyalkyl polyacrylate compounds of formula (VIII) with a diene, to produce the corresponding Diels-Alder adduct. Suitable solvents for this reaction are the common solvents used in the art to carry out Diels-Alder reactions, as described above. Illustrative of these compounds are those represented by formula (IX), which are obtained by reaction of the hydroxyalkyl polyacrylate compounds of formula (VIII) with cyclopentadiene to produce the corresponding adducts that contain polynorbornene moieties, as shown in the following scheme, wherein R1, R2, R3, and W are as defined in the foregoing, and m is an integer from 2 to 12:

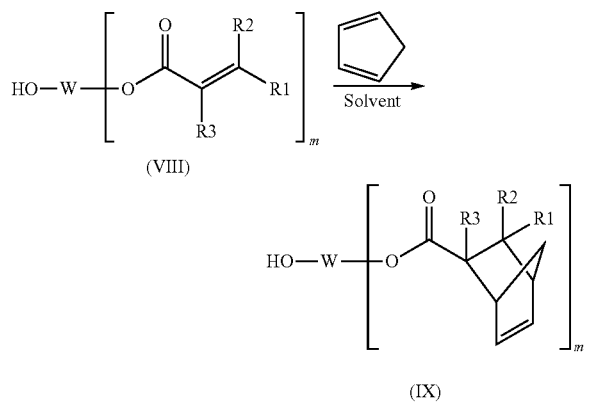

It is to be understood that, as contemplated herein, various other hydroxyalkyl polyacrylate compounds may be used in the Diels-Alder reaction with the various dienes (e.g., cyclopentadiene). Illustrative of such other hydroxyalkyl polyacrylate compounds are the following examples represented by formulae (X) and (XI) below:

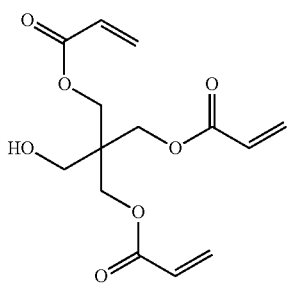

(X)

(XI)

Specifically, in the case of the reaction of (X) with cyclopentadiene, a Diels-Alder adduct is obtained that contains three norbornene moieties; likewise, in the case of the reaction of (XI) with cyclopentadiene, a Diels-Alder adduct is obtained that contains five norbornene moieties.

In another embodiment of the invention, Star monomers containing multiple norbornene groups are described herein. These Star monomers may be obtained by the reaction of the hydroxyalkyl polynorbornene compounds represented by the formula (IX) with a tris(isocyanatoaryl)methane of formula (III), under conditions similar to those described earlier. Illustratively, the polynorbornene-containing hydroxyalkyl compounds obtained from the reactions of (X) and (XI), respectively, with cyclopentadiene are further reacted with tris(isocyanatoaryl)methane of formula (III) to produce the corresponding Star monomers.

In another embodiment of the invention, polynorbornene-polyurethane (PNUP) aerogel polymers are described herein. These PNUP aerogel polymers are obtained via a process wherein the norbornene-containing Star monomers represented by formula (VII), or the norbornene-containing Star monomers described in the previous paragraph, are polymerized under ring-opening metathesis polymerization conditions. Any of a variety of suitable conditions for ring-opening metathesis polymerization that are well-known in the art may be used. Illustrative of these conditions are as follows:

First and second generation Grubbs catalysts (GC-I and GC-II) may be used,

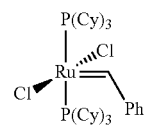

GC-I

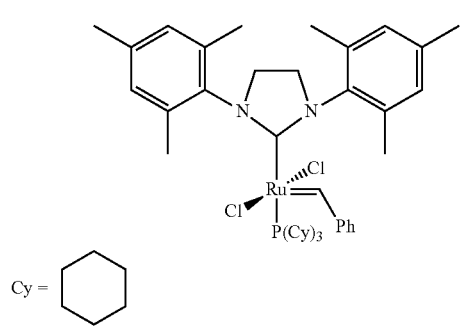

GC-II

Cy = which offer the advantages of tolerance to moisture, oxygen, protic solvents and functional groups. GC-1 has been used in toluene, GC-II has been used in toluene, acetone, tetrahydrofyran, THF and methanol. Further and alternatively, the ring-opening metathesis polymerization process may be carried out in the presence of chain extenders that are known to persons skilled in the relevant art. The following bisnorborneneacyloxyethyl carbonate compound (XII) is illustrative of such chain extenders.

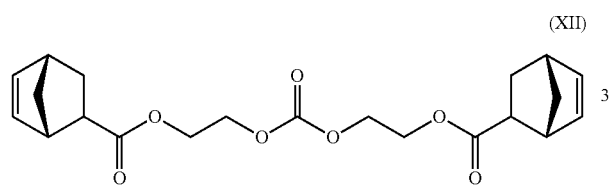

(XII)

In another embodiment, the aerogels of the invention herein are porous, low-density 3D assemblies of nanoparticles with large surface-to-volume ratios. In one aspect, the aerogels possess flexibility that makes them particularly attractive materials for thermal insulation. The flexible aerogels herein were characterized at the molecular level (solid phase $^{13}C$ NMR), nanoscopic level (SEM, SAXS), and macroscopic level (compression and 3-point bending). The lower density PUAC aerogels (0.14 g cm$^{-3}$) consist of large primary particles (88 nm in diameter) and are macroporous and flexible. The higher density PUAC aerogels (0.66 g cm$^{-3}$) consist of smaller particles (18 nm in diameter), and are rigid and mechanically strong.

While the novel technology herein has been illustrated and described in detail in the foregoing description, and in the following examples and figures, the same is to be considered as illustrative and not restrictive in character. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

EXAMPLES

The following examples further illustrate specific embodiments of the invention. However, the following examples should not be interpreted in any way to limit the invention.

MATERIALS. All reagents and solvents were used as received unless noted otherwise. 2-Hydroxyethyl acrylate (HEA), 2,2'-azobisisobutyronitrile (AIBN) and dibutyltin dilaurate (DBTDL) were purchased from Sigma-Aldrich Anhydrous acetone was purchased from Fisher Scientific. Siphon-grade $CO_2$ was purchased from Ozark Gas Co. Tris(4-isocyanatophenyl)-methane (TIPM) (27% w/w solution in ethyl acetate) was obtained from Bayer Corporation USA (TIPM is referred to by Bayer Corporation as Desmodur RE).

Example 1

Illustrative preparation of urethane-acrylate (UAC) Star monomers. A urethane-acrylate Star monomer was synthesized via reaction of TIPM (1 mmol) with HEA (3 mmol) using DBTDL (5 μL) as a catalyst in anhydrous acetone (see Scheme 1). The reaction mixture was stirred at room temperature for 30 min. The quantity of anhydrous acetone was varied depending upon the desirable weight percent of solids in the solution. The UAC Star monomer can be isolated, recrystallized from $CH_2Cl_2$/hexane, and fully characterized. However, for routine preparation of aerogels, gelation was induced in one pot by adding a radical initiator, as described in the following example.

Scheme 1

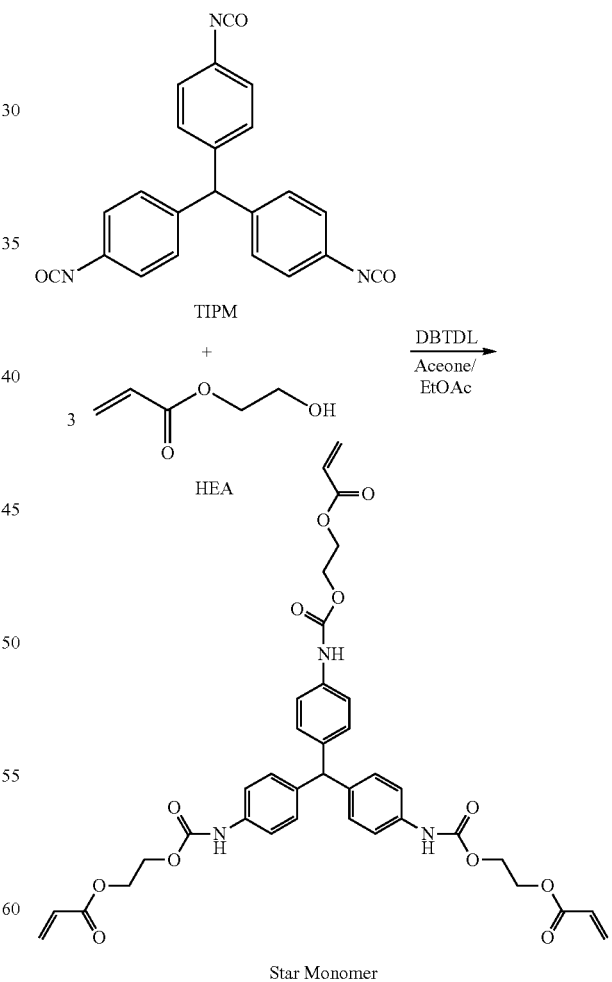

Star Monomer

The UAC Star monomer was characterized by $^{13}C$ NMR, the spectrum of which is shown in FIG. 1. Peak f (154 ppm) corresponds to the carbonyl group of the urethane linkage.

Figure 2:
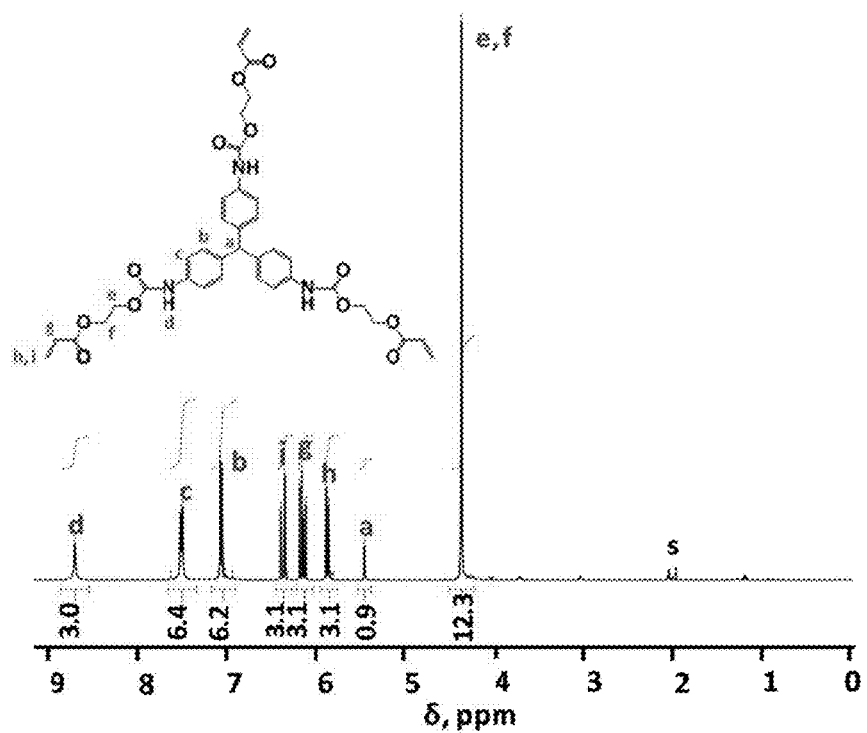
FIG. 2 shows the $^1H$ NMR spectrum of the UAC Star monomer of Example 1, in $CD_3COCD_3$.
Figure 3:
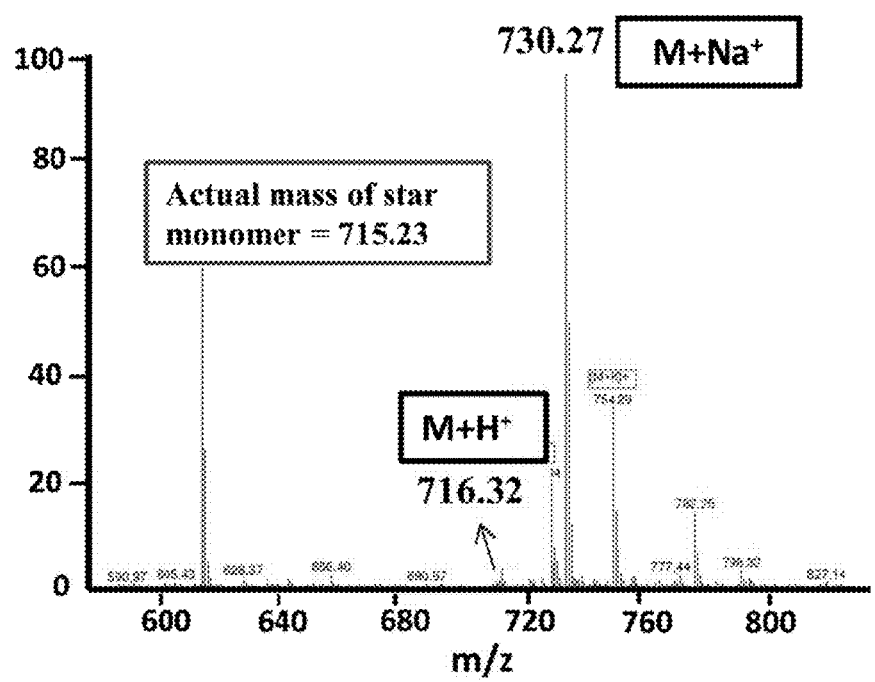
FIG. 3 shows the high resolution mass spectrum of the UAC Star monomer of Example 1.

Peaks j and k correspond to the acrylate moieties, which were used for free radical polymerization. The UAC Star monomer was also characterized by $^1$H NMR; the spectrum is shown in FIG. 2. The UAC Star monomer was also characterized by high resolution mass spectroscopy; the data is shown in FIG. 3.

Example 2

Figure 17:
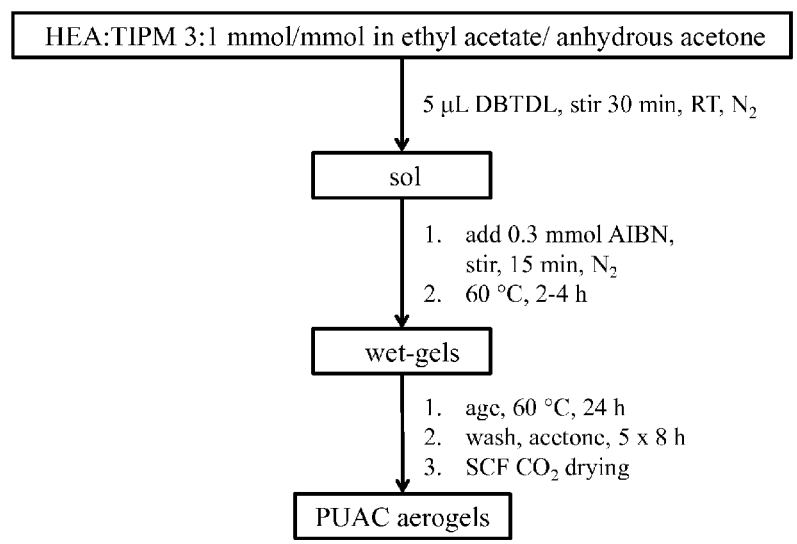
FIG. 17 describes an illustrative preparation of PUAC aerogels.

Illustrative preparation of PUAC aerogels. A UAC Star monomer was prepared as described in the previous example. Gelation was induced in one pot by adding AIBN (0.3 mmol) into the reaction mixture containing the UAC Star monomer, followed by transferring into molds and heating at 60° C. for 2-4 h (see FIG. 17). Wet-gels were aged in their molds for 24 h at 60° C., then transferred in acetone, washed 5 times, 8 h per wash, and finally were dried using SCF $CO_2$ to produce the PUAC aerogels. Polypropylene vials (4 mL, Wheaton polypropylene Omnivials, Part No. 225402, 1 cm in diameter), or polypropylene centrifuge tubes (50 mL, Fisher Scientific, Cat. No. 06-443-18, 2.8 cm in diameter) were used as molds. The PUAC aerogels are referred to herein as 'xx-PUAC', where 'xx' denotes percent weight of monomers in the solution.

Figure 4:
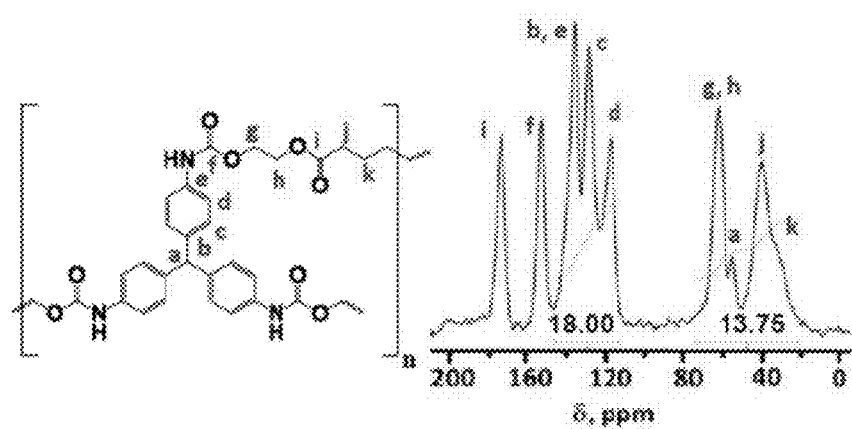
FIG. 4 shows the solid phase $^{13}C$ NMR spectrum of a 9-PUAC aerogel sample prepared as described in Example 2.

Solid phase $^{13}$C NMR was used to confirm formation of the PUAC polymer and to determine whether all the double bonds of the Star monomer had reacted by free radical polymerization. FIG. 4 shows the solid phase $^{13}$C NMR of a 9-PUAC prepared as described above. The relative ratio of aromatic carbons (110-145 ppm) to aliphatic carbons (20-75 ppm) was found to be close to the theoretical value (1.31:1.00 vs 1.38:1.00, respectively), thus confirming complete reaction.

Example 3

Figure 5:
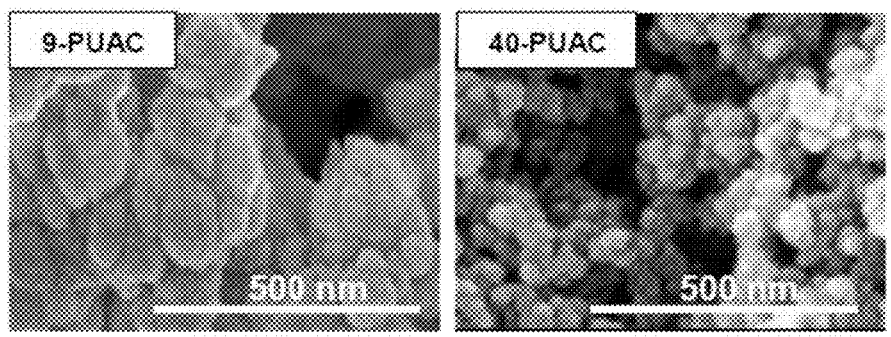
FIG. 5 shows SEM images of 9-PUAC and 40-PUAC, respectively.

Comparison of PUAC aerogels from the lowest Star monomer concentration (9-PUAC) with PUAC aerogels from the highest Star monomer concentration (40-PUAC). The PUACs were prepared as described in the previous example. It was found that 9-PUACs were flexible, while 40-PUACs were rigid. The SEM images of 9-PUAC and 40-PUAC are displayed in FIG. 5, which show the following data: SEM of 9-PUAC: $\rho_b$=0.135±0.004 g cm$^{-3}$, porosity=90% v/v; SEM of 40-PUAC: $\rho_b$=0.662±0.004 g cm$^{-3}$, porosity=50% v/v. At lower monomer concentrations, the polymer chains are expected to grow longer resulting late phase separation and formation of larger primary particles (88 nm in diameter by SAXS for 9-PUAC). At higher monomer concentrations, early phase separation leads to formation of smaller primary particles (18 nm in diameter by SAXS for 40-PUAC). Aggregation of primary particles in case of 40-PUAC yields clusters of secondary and tertiary particles (by SAXS). Therefore, 9-PUAC aerogels have lower inter-particle connectivity than 40-PUAC.

Example 4

Figure 6:
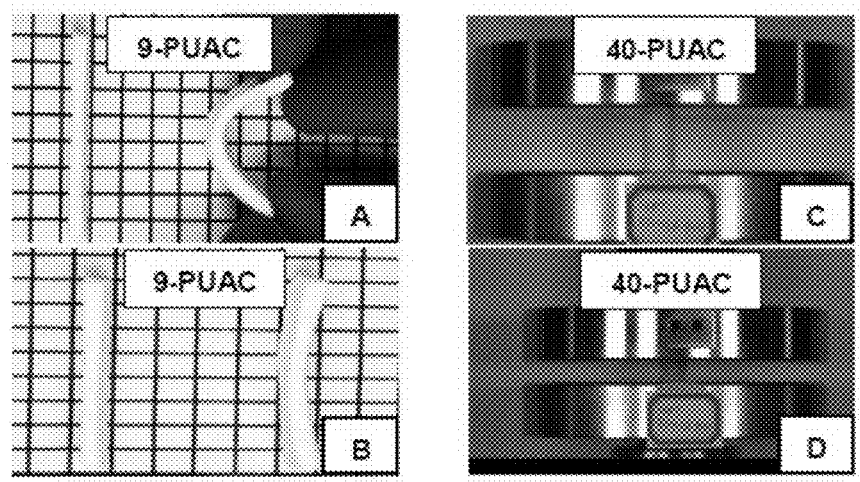
FIG. 6 shows a comparison of the mechanical behavior of 9-PUAC and 40-PUAC aerogels. 9-PUAC: (A) Flexing, (B) after releasing the stress. 40-PUAC: (C) Before compression, (D) after compression using an Instron 4469 Universal Testing Machine.

Comparison of the Mechanical Behavior of 9-PUAC and 40-PUAC aerogels. A comparison of the mechanical behavior of 9-PUAC and 40-PUAC aerogels is shown in FIG. 6: 9-PUAC: (A) Flexing, (B) after releasing the stress. 40-PUAC: (C) Before compression, (D) after compression using an Instron 4469 Universal Testing Machine. It was found that 9-PUAC is flexible and when stress is released, it practically recovers its original shape.

Example 5

Figure 7:
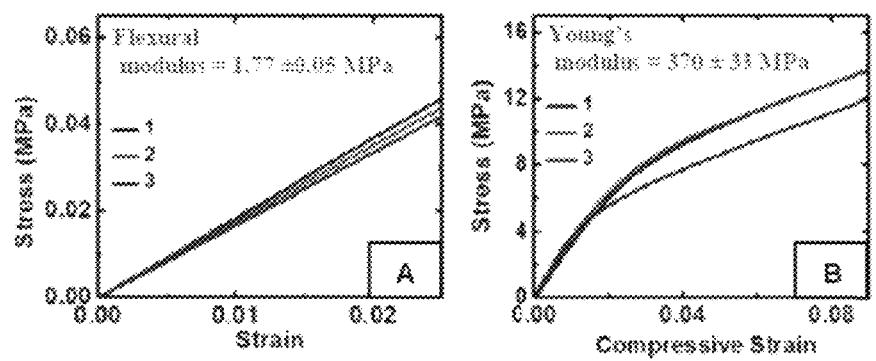
FIG. 7 shows flexibility data for 9-PUAC and 40-PUAC aerogels.

Flexibility of PUAC Aerogels. The flexibility of 9-PUAC was formally characterized with 3-point bending using a Dynamic Mechanical Analyzer (FIG. 7). (A) Stress-strain curves of 9-PUAC aerogels via a 3-point bending test (3 samples—only the early part of the curve is shown). (B) Stress-strain curves of 40-PUAC aerogels via compression testing (3 samples—only the early part of the curve is shown). With a higher inter-particle connectivity, 40-PUAC aerogels are rigid and mechanically strong (see FIG. 6D). The ultimate compressive strength, the compressive Young's modulus and the specific energy absorption were found to be equal to 175 MPa, 370 MPa and 45 J g$^{-1}$, respectively (see FIG. 7B).

Example 6

Illustrative preparation of PUAC aerogels with inclusion of ethyleneglycol dimethacrylate (EGDMA) or hexamethylene diacrylate (HMDA) as chain extenders. A UAC Star monomer was prepared exactly as described in Example 1 above. EGDMA or HMDA (0.75 mmol) was added to the UAC Star monomer solution. Gelation with AIBN, and subsequent aging of the wet-gels in molds, and drying using SCF $CO_2$ were done exactly as described in the procedure of Example 2 above. This provided the desired ethyleneglycol diacrylate extended PUAC (PUAC-EG) or the hexamethylene diacrylate extended PUAC (PUAC-HD).

Example 7

Figure 8:
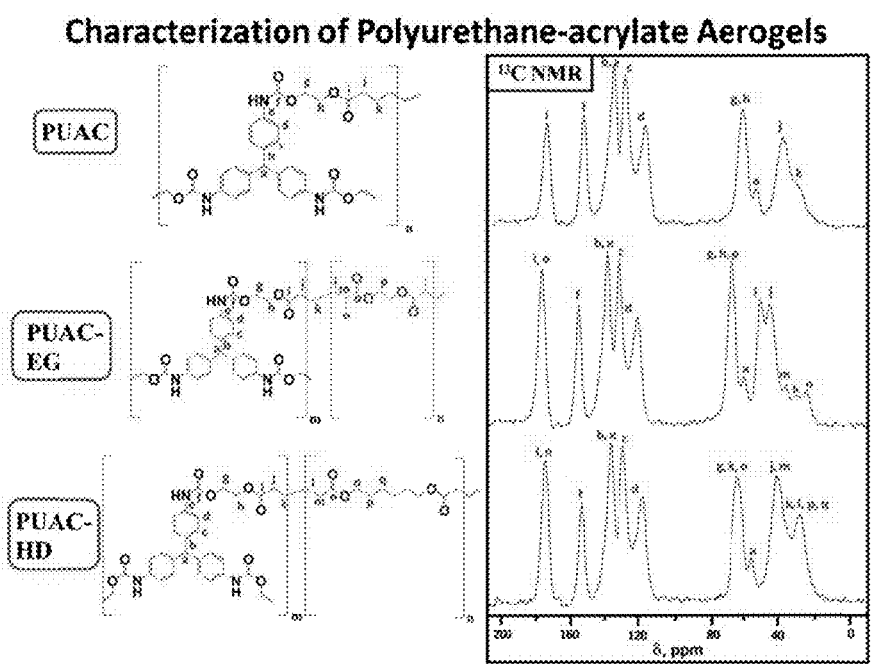
FIG. 8 shows a comparative characterization by solid phase $^{13}C$ NMR of PUAC, PUAC-EG, and PUAC-HD.

Comparative characterization by solid phase $^{13}$C NMR of PUAC, PUAC-EG, and PUAC-HD. FIG. 8 shows the comparative $^{13}$C NMR spectra of PUAC, PUAC-EG, and PUAC-HD, showing that the chain extenders have been incorporated in the material in the prescribed molar ratio.

Example 8

Figure 9:
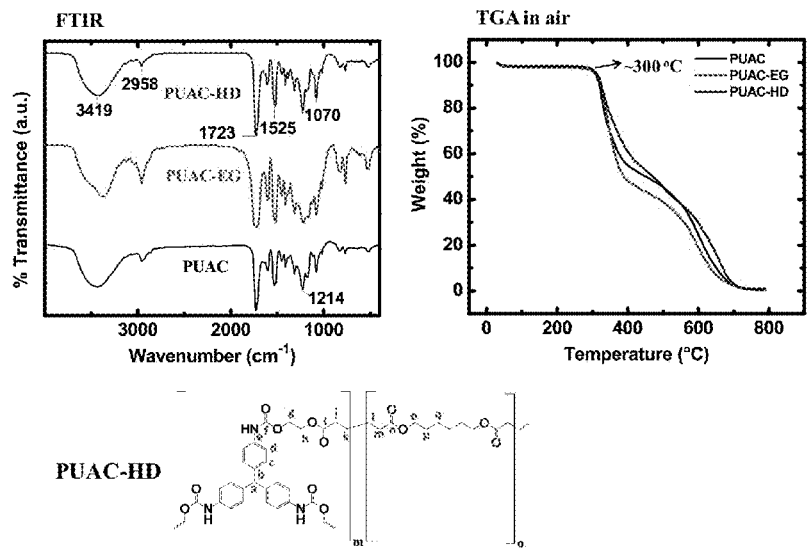
FIG. 9 shows a comparative characterization by FTIR and TGA of PUAC, PUAC-EG, and PUAC-HD.

Comparative characterization by FTIR and thermogravimetric analysis (TGA) of PUAC, PUAC-EG, and PUAC-HD. FIG. 9 shows a comparison of the FTIR spectra and TGA traces of PUAC, PUAC-EG, and PUAC-HD, showing the chain extenders do not alter substantially the functional group footprint or the thermal behavior of the basic PUAC materials.

Example 9

Figure 10:
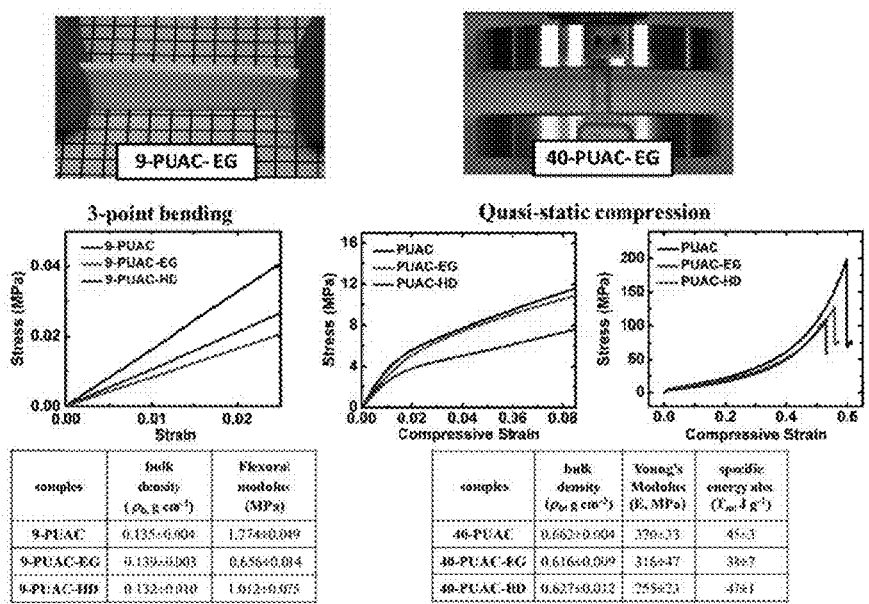
FIG. 10 shows a comparison of the mechanical properties of PUAC, PUAC-EG, and PUAC-HD.

Comparative mechanical characterization of PUAC, PUAC-EG, and PUAC-HD. FIG. 10 shows a comparison of the mechanical properties of PUAC, PUAC-EG, and PUAC-HD, showing that chain extenders change substantially the flexural moduli of the material, but not its compressive behavior.

Example 10

Figure 11:
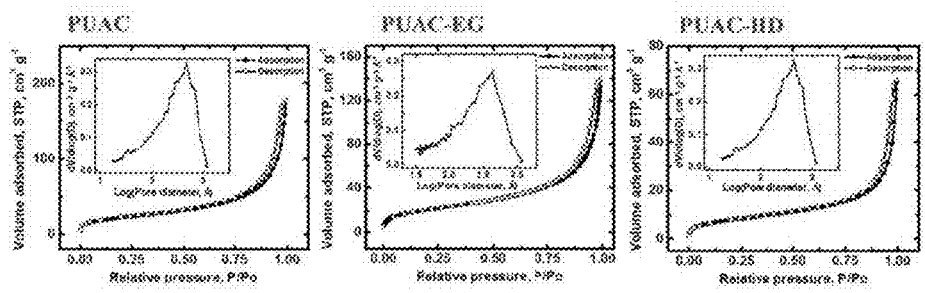
FIG. 11 shows a comparison of properties of PUAC, PUAC-EG, and PUAC-HD prepared at 9% w/w concentration of Star monomer precursors.

Comparison of properties of PUAC, PUAC-EG, and PUAC-HD prepared at 9% w/w concentration of Star monomer precursors. FIG. 11 displays various comparative properties related to the porous structure of the PUAC, PUAC-EG, and PUAC-HD prepared at 9% w/w concentration of Star monomer precursors. For comparative bulk densities, progressively longer chain extenders give larger particles and significantly reduced surface areas.

Example 11

Figure 12:
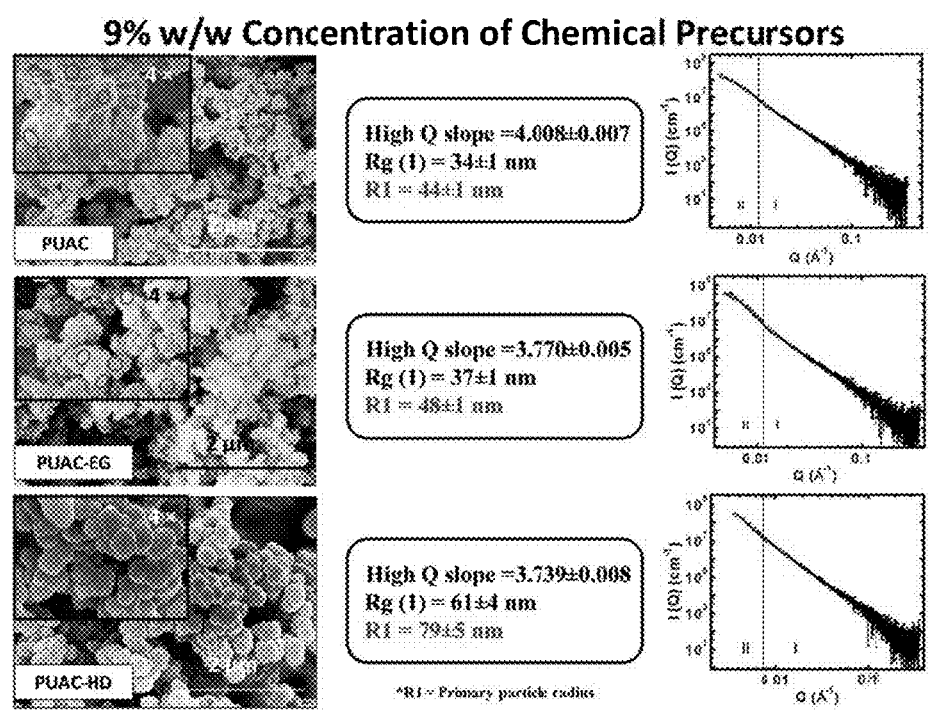
FIG. 12 shows a comparison of particle properties of PUAC, PUAC-EG, and PUAC-HD prepared at 9% w/w concentration of Star monomer precursors.

Comparison of particle properties of PUAC, PUAC-EG, and PUAC-HD prepared at 9% w/w concentration of Star monomer precursors. FIG. 12 displays comparative particle sizes determined with small angle x-ray scattering and SEM of the PUAC, PUAC-EG, and PUAC-HD prepared at 9% w/w concentration of Star monomer precursors, showing a generally good agreement between primary particle sizes with those calculated from gas sorption data (refer to FIG. 11), indicating absence of closed porosity.

Example 12

Figure 13:
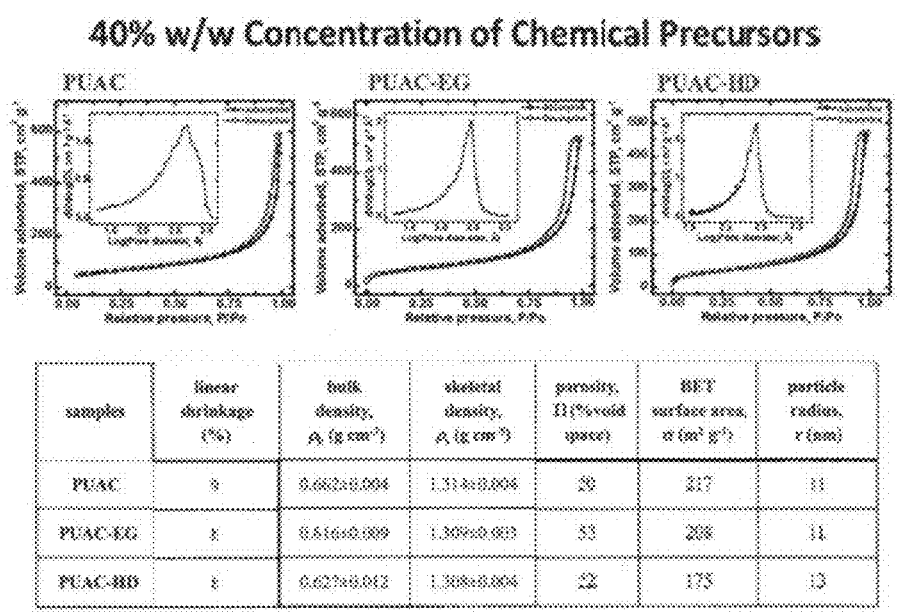
FIG. 13 shows a comparison of properties of PUAC, PUAC-EG, and PUAC-HD prepared at 40% w/w concentration of Star monomer precursors.

Comparison of properties of PUAC, PUAC-EG, and PUAC-HD prepared at 40% w/w concentration of Star monomer precursors. FIG. 13 displays various comparative properties related to the porous structure of the PUAC, PUAC-EG, and PUAC-HD prepared at 40% w/w concentration of Star monomer precursors. For comparative bulk densities, particle sizes are not affected by the presence of chain extenders.

Example 13

Figure 14:
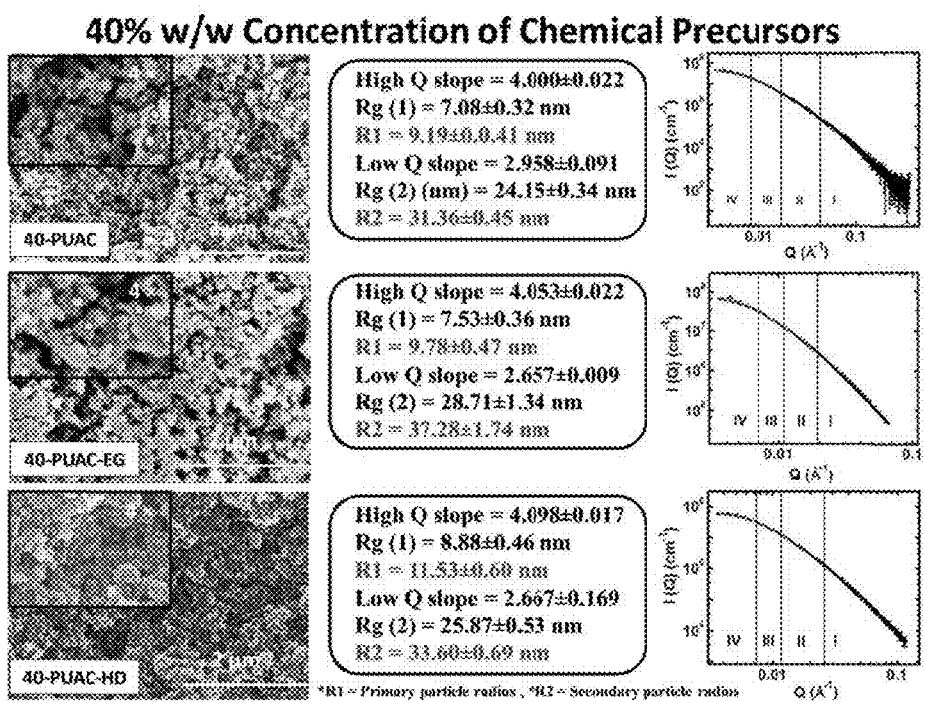
FIG. 14 shows a comparison of particle properties of PUAC, PUAC-EG, and PUAC-HD prepared at 40% w/w concentration of Star monomer precursors.

Comparison of particle properties of PUAC, PUAC-EG, and PUAC-HD prepared at 40% w/w concentration of Star monomer precursors. FIG. 14 displays comparative particle sizes determined with small angle x-ray scattering and SEM of the PUAC, PUAC-EG, and PUAC-HD prepared at 40% w/w concentration of Star monomer precursors, showing a generally good agreement between primary particle sizes with those calculated from gas sorption data (refer to FIG. 13), indicating absence of closed porosity Example 14

Figure 15:
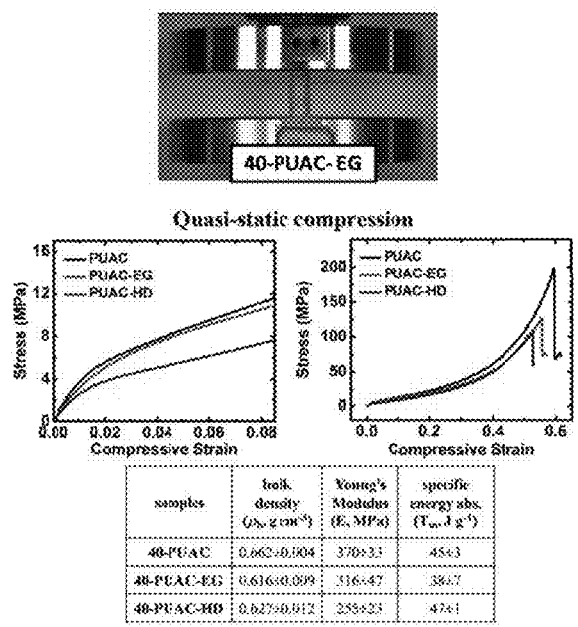
FIG. 15 shows a comparison of quasi-static compression properties of PUAC, PUAC-EG, and PUAC-HD.

Comparison of quasi-static compression properties of PUAC, PUAC-EG, and PUAC-HD. FIG. 15 displays comparative quasi-static compression data of PUAC, PUAC-EG, and PUAC-HD. For comparative densities, the Young's modulus decreases and flexibility increases for longer chain extenders, but the overall energy absorption capability remains about the same.

Example 15

Figure 16:
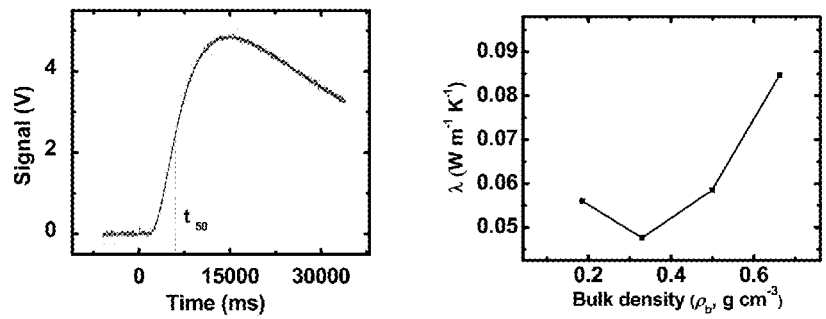
FIG. 16 displays thermal conductivity properties of PUAC aerogels.

Thermal conductivity properties of PUAC aerogels. FIG. 16 displays thermal conductivity data of PUAC aerogels. On the left, it shows raw data of heat transfer across an aerogel disk using a laser flash method. On the right, it shows the variation of thermal conductivity, $\lambda$, with bulk density. 20-PUAC samples are about as good thermal insulators as glass wool (0.047 versus 0.040 $W\ m^{-1}\ K^{-1}$).

Example 16

Illustrative preparation of Star monomers containing norbornene groups. To a solution of 2-hydroxyethyl acrylate in toluene is added a solution of cyclopentadiene in toluene, the mixture is stirred under conditions known in the art to be suitable for Diels-Alder reaction, and the reaction between the alkene and diene is monitored until formation of the Diels-Alder adduct is complete. The resultant norbornene-containing hydroxyl compound is isolated using standard organic chemistry procedures. Subsequently, this norbornene-containing hydroxyl compound is subjected to reaction with TIPM in the presence of DBTDL as a catalyst in anhydrous acetone, following the procedure described in Example 1 above, thus producing the corresponding tris (norbornene)-containing Star monomer.

Additional examples of the preparation of norbornene-containing Star monomers following the procedure described herein are displayed in the following scheme, wherein n is an integer that is equal to 3, 9, or 15. The polynorbornene-containing Star monomer 15-NB shown below is obtained in the case where n=15:

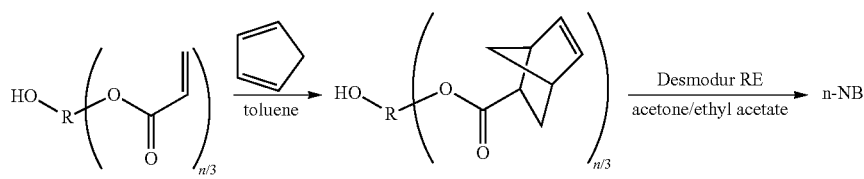

whereas:

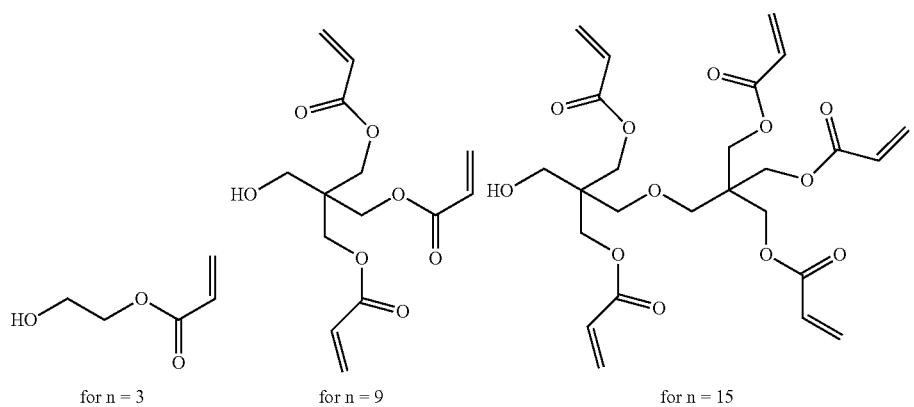

for n = 3      for n = 9      for n = 15

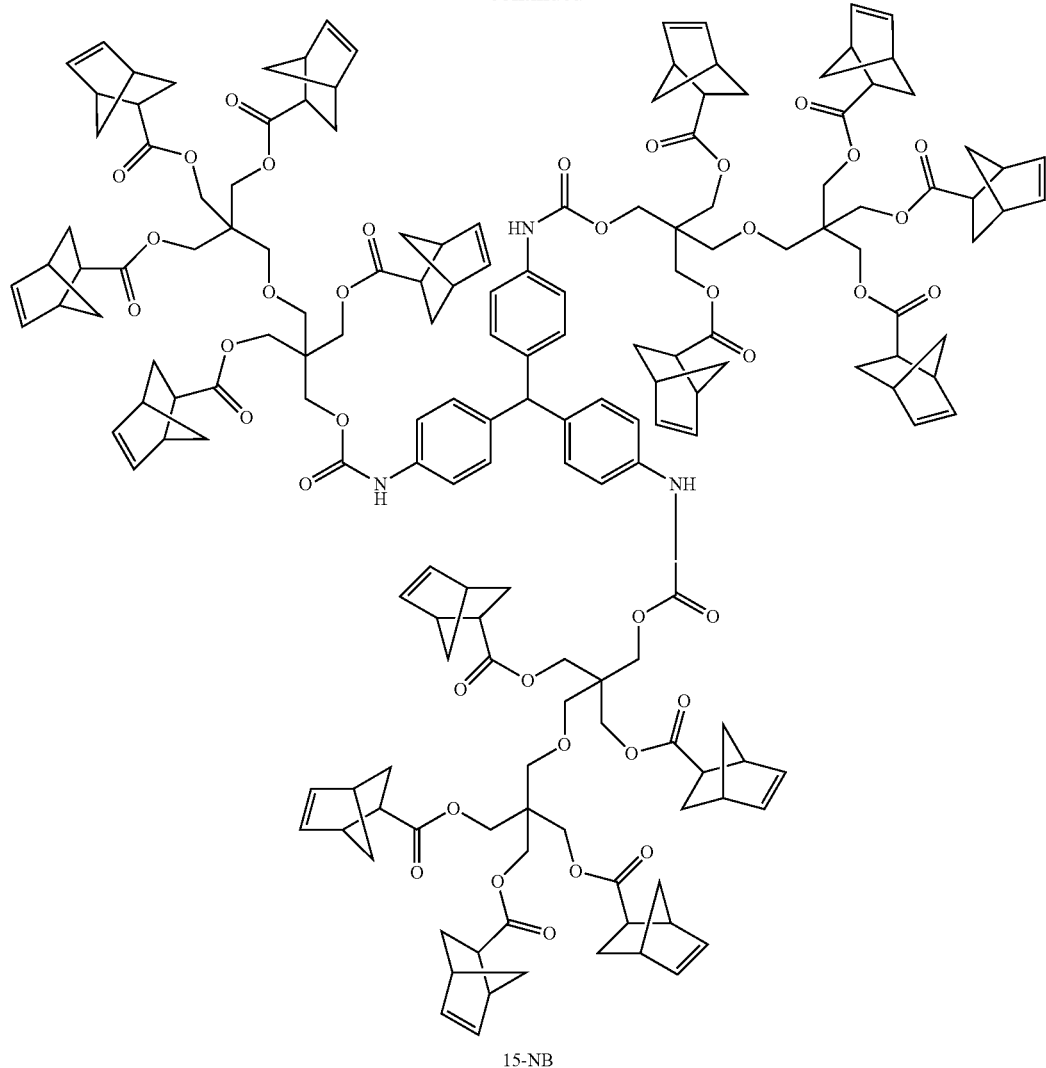

15-NB

What is claimed is:

1. A nanoporous material comprising a polyurethane-acrylate polymer formed by the polymerization of a urethane-acrylate star monomer of the formula (I):

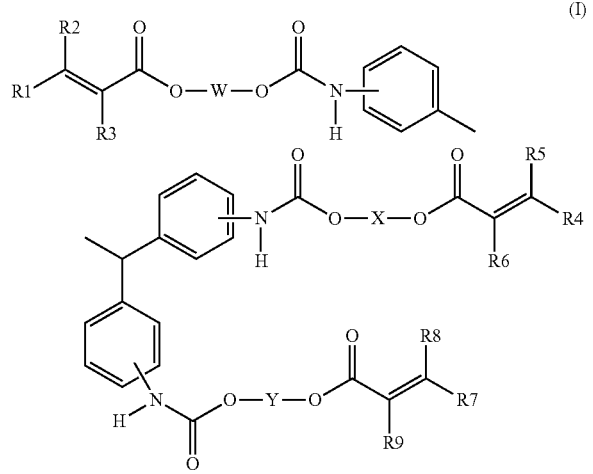

in the presence of a polymerization catalyst at 60° C. for 2-4 h, to give a wet gel, followed by aging of the wet gel for 24 h at 60° C., washing five times with acetone for 8 h per wash, and drying with supercritical fluid $CO_2$;

wherein the nitrogen atoms of the urethane moieties in the urethane-acrylate star monomer of the formula (I) are independently attached to their respective aryl rings at the 2, 3, or 4-positions of the aryl rings;

wherein each of W, X, and Y independently represents a $C_1$-$C_6$ straight chain alkyl group or a $C_1$-$C_6$ branched alkyl group;

wherein each of R1-R9 is independently a hydrogen, a $C_1$-$C_6$ straight chain alkyl group, or a $C_1$-$C_6$ branched alkyl group; and, wherein the material is an aerogel.

2. The material of claim 1, wherein the polymerization catalyst is a free radical initiator.

3. The material of claim 2, wherein the free radical initiator is 2,2'-azobisisobutyronitrile.

4. The material of claim 1 wherein in the polyurethane-acrylate polymer the nitrogen atoms of the urethane moieties are attached to their respective aryl rings at the 4-positions of the aryl rings.

5. The material of claim 1 wherein in the polyurethane-acrylate polymer W=X=Y=CH$_2$CH$_2$.

6. The material of claim 1 wherein in the polyurethane-acrylate polymer each of R1-R9 is a hydrogen.

7. The material of claim 1 wherein in the polyurethane-acrylate polymer the nitrogen atoms of the urethane moieties are attached to their respective aryl rings at the 4-positions of the aryl rings; wherein W=X=Y=CH$_2$CH$_2$; and wherein each of R1-R9 is a hydrogen.

8. A process for the preparation of the nanoporous material of claim 1, the process comprising the step of treating a mixture of the urethane-acrylate star monomer in an organic solvent with a polymerization catalyst at 60° C. for 2-4 h, to give a wet gel, followed by the step of aging of the wet gel for 24 h at 60° C., the step of washing five times with acetone for 8 h per wash, and the step of drying with supercritical fluid CO$_2$.

9. The process of claim 8, wherein the organic solvent is selected from the group consisting of a ketone solvent, an ester solvent, and a combination thereof.

10. The process of claim 8, wherein the organic solvent is acetone, ethyl acetate, or a combination thereof.

11. A one-pot process for the preparation of the nanoporous material of claim 1, the process comprising the steps of:

(a) preparing a solution of the urethane-acrylate star monomer by mixing a tris(isocyanatophenyl)methane of formula (III)

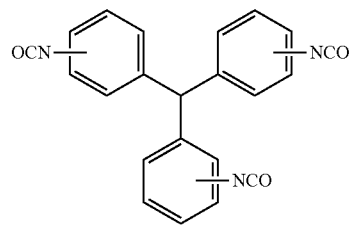

(III)

with three molar equivalents of a hydroxyacrylate compound of the formula (IV)

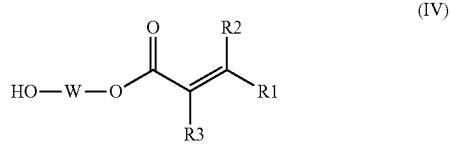

(IV)

in an organic solvent;

(b) treating the solution of the urethane-acrylate star monomer with a polymerization catalyst at 60° C. for 2-4 h to give a wet gel;

(c) aging of the wet gel for 24 h at 60° C.;

(d) washing five times with acetone for 8 h per wash; and, (e) drying with supercritical fluid CO$_2$;

wherein each of R1-R3 is independently a hydrogen, a C$_1$-C$_6$ straight chain alkyl group, or a C$_1$-C$_6$ branched alkyl group.

12. A nanoporous material comprising a polyurethane-acrylate polymer formed by the copolymerization of a urethane-acrylate star monomer of the formula (I):

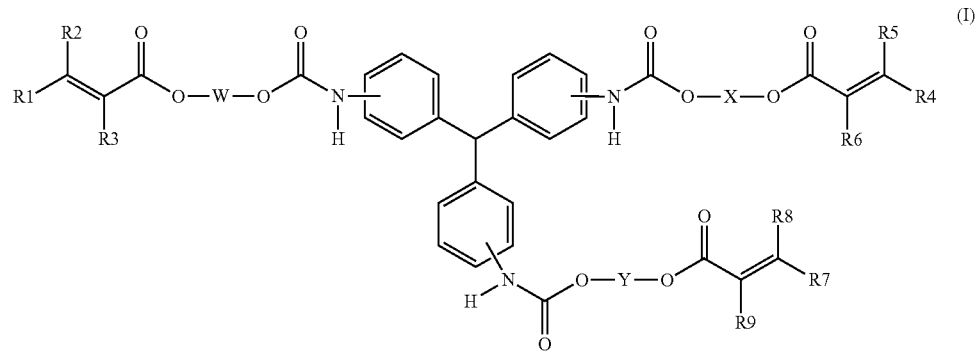

(I)

with a polymerization chain extender, in the presence of a polymerization catalyst at 60° C. for 2-4 h, to give a wet gel, followed by aging of the wet gel for 24 h at 60° C., washing five times with acetone for 8 h per wash, and drying with supercritical fluid $CO_2$;

wherein the nitrogen atoms of the urethane moieties in the urethane-acrylate star monomer of the formula (I) are independently attached to their respective aryl rings at the 2, 3, or 4-positions of the aryl rings;

wherein each of W, X, and Y independently represents a $C_1$-$C_6$ straight chain alkyl group or a $C_1$-$C_6$ branched alkyl group;

wherein each of R1-R9 is independently a hydrogen, a $C_1$-$C_6$ straight chain alkyl group, or a $C_1$-$C_6$ branched alkyl group; and, wherein the material is an aerogel.

13. The material of claim 12, wherein the polymerization chain extender is a compound comprising from 2 to 4 acrylate groups or from 2 to 4 methacrylate groups, or a combination thereof.

14. The material of claim 13, wherein the chain extender is a compound comprising 2 acrylate groups.

15. The material of claim 14, wherein the chain extender is a diacrylate compound of formula (V):

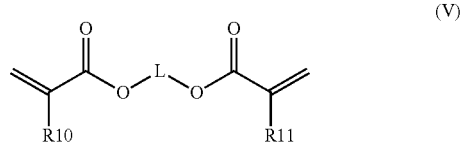

wherein L represents a linker group selected from $C_1$-$C_{12}$ straight chain or branched chain alkyl, alkoxyalkyl, alkoxycarbonylalkyl, and alkoxycarboxyalkyl; and wherein each of R10 and R11 is independently a hydrogen, a $C_1$-$C_6$ straight chain alkyl group or a $C_1$-$C_6$ branched alkyl group.

16. The material of claim 15, wherein the chain extender is a diacrylate compound selected from the group consisting of:

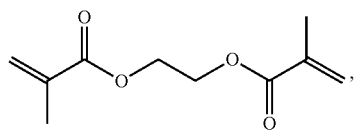

Ethylene glycol dimethacrylate (EG)

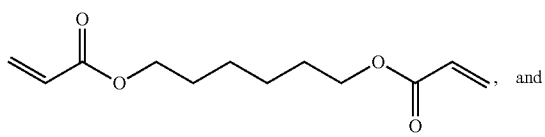

1,6-Hexanediol diacrylate (HD)

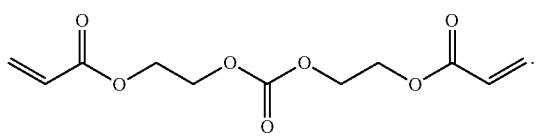

Bisacryloylethyl carbonate

17. The material of claim 12 wherein in the polyurethane-acrylate polymer the nitrogen atoms of the urethane moieties are attached to their respective aryl rings at the 4-positions of the aryl rings.

18. The material of claim 12 wherein in the polyurethane-acrylate polymer W=X=Y=$CH_2CH_2$.

19. The material of claim 12 wherein in the polyurethane-acrylate polymer each of R1-R9 is a hydrogen.

20. The material of claim 12 wherein in the polyurethane-acrylate polymer the nitrogen atoms of the urethane moieties are attached to their respective aryl rings at the 4-positions of the aryl rings; wherein W=X=Y=$CH_2CH_2$; and wherein each of R1-R9 is a hydrogen.

21. A process for preparing the nanoporous material of claim 12, the process comprising the step of treating a mixture of the urethane-acrylate star monomer and the chain extender in an organic solvent with a polymerization catalyst at 60° C. for 2-4 h, to give a wet gel, followed by the step of aging of the wet gel for 24 h at 60° C., the step of washing five times with acetone for 8 h per wash, and the step of drying with supercritical fluid $CO_2$.

22. The process of claim 21, wherein the organic solvent is selected from the group consisting of a ketone solvent, an ester solvent, and a combination thereof.

23. The process of claim 21, wherein the organic solvent is acetone, ethyl acetate, or a combination thereof.

24. A one-pot process for the preparation of the nanoporous material of claim 12, the process comprising the steps of:
(a) preparing a solution of the urethane-acrylate star monomer by mixing a tris(isocyanatophenyl)methane of formula (III)

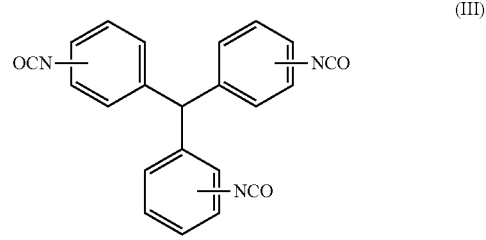

with three molar equivalents of a hydroxyacrylate compound of formula (IV)

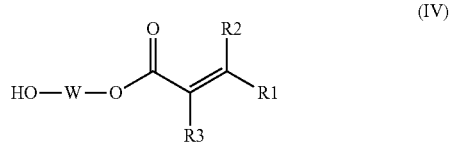

in an organic solvent;
(b) adding a chain extender;
(c) treating the solution of the urethane-acrylate star monomer and the chain extender with a polymerization catalyst at 60° C. for 2-4 h to give a wet gel;
(d) aging of the wet gel for 24 h at 60° C.;
(e) washing five times with acetone for 8 h per wash; and,
(f) drying with supercritical fluid $CO_2$;
wherein each of R1-R3 is independently a hydrogen, a $C_1$-$C_6$ straight chain alkyl group, or a $C_1$-$C_6$ branched alkyl group.

25. A nanoporous material comprising a polyurethane-acrylate polymer of the formula (II):

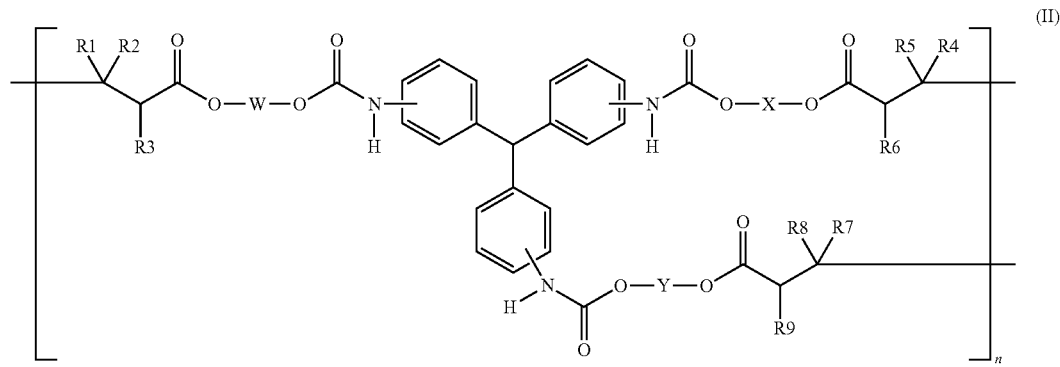

wherein the nitrogen atoms of the urethane moieties are independently attached to their respective aryl rings at the 2, 3, or 4-positions of the aryl rings;
wherein each of W, X, and Y independently represents a $C_1$-$C_6$ straight chain alkyl group or a $C_1$-$C_6$ branched alkyl group;
wherein each of R1-R9 is independently a hydrogen, a $C_1$-$C_6$ straight chain alkyl group or a $C_1$-$C_6$ branched alkyl group;
wherein n is an integer greater than 1; and
wherein the material is an aerogel.

26. The material of claim 25 wherein the nitrogen atoms of the urethane moieties of the polyurethane-acrylate polymer are attached to their respective aryl rings at the 4-positions of the aryl rings.

27. The material of claim 25 wherein in the polyurethane-acrylate polymer W=X=Y=$CH_2CH_2$.

28. The material of claim 25 wherein in the polyurethane-acrylate polymer each of R1-R9 is a hydrogen.

29. The material of claim 25 wherein in the polyurethane-acrylate polymer the nitrogen atoms of the urethane moieties are attached to their respective aryl rings at the 4-positions of the aryl rings; wherein W=X=Y=$CH_2CH_2$; and wherein each of R1-R9 is a hydrogen.

* * * * *